(12) United States Patent
Markey et al.

(10) Patent No.: US 9,409,027 B2
(45) Date of Patent: Aug. 9, 2016

(54) CALIBRATION OF CURRENT SOURCES AND SINKS IN A STIMULATING MEDICAL DEVICE

(75) Inventors: Matthew Markey, Oateley (AU); Yashodhan Moghe, Hurstville (AU)

(73) Assignee: Cochlear Limited, Macquarie University, NSW (AU)

( * ) Notice: Subject to any disclaimer, the term of this patent is extended or adjusted under 35 U.S.C. 154(b) by 45 days.

(21) Appl. No.: 13/496,984

(22) PCT Filed: Sep. 20, 2010

(86) PCT No.: PCT/IB2010/054246
§ 371 (c)(1),
(2), (4) Date: Apr. 11, 2012

(87) PCT Pub. No.: WO2011/033489
PCT Pub. Date: Mar. 24, 2011

(65) Prior Publication Data
US 2012/0191146 A1    Jul. 26, 2012

(30) Foreign Application Priority Data

Sep. 18, 2009 (AU) .............................. 2009217394

(51) Int. Cl.
*A61N 1/36* (2006.01)
*A61N 1/372* (2006.01)
*A61N 1/02* (2006.01)
*H03M 1/10* (2006.01)

(52) U.S. Cl.
CPC .............. *A61N 1/372* (2013.01); *A61N 1/025* (2013.01); *A61N 1/36* (2013.01); *H03M 1/1009* (2013.01); *A61N 1/36032* (2013.01)

(58) Field of Classification Search
CPC .......... A61N 1/02; A61N 1/025; A61N 1/372
USPC ............................ 607/2, 45, 57, 64
See application file for complete search history.

(56) References Cited

U.S. PATENT DOCUMENTS

| 4,706,674 | A | 11/1987 | Dieken et al. |
| 4,917,093 | A | 4/1990 | Dufresne et al. |
| 6,035,237 | A | 3/2000 | Schulman et al. |
| 6,181,969 | B1 * | 1/2001 | Gord ................................ 607/59 |
| 6,363,277 | B1 * | 3/2002 | Dooley et al. ...................... 607/9 |
| 7,539,538 | B2 | 5/2009 | Parramon et al. |

(Continued)

FOREIGN PATENT DOCUMENTS

GB    2 449 546    11/2008

OTHER PUBLICATIONS

International Search Report, International Application No. PCT/IB2010/054246, mailed on Jun. 29, 2011 (3 Pages).
European Search Report and Opinion for European Application No. 10816789.1 mailed Jan. 4, 2013 (6 pages).

*Primary Examiner* — Joseph Dietrich (57) ABSTRACT

A stimulating medical device, comprising a plurality of electrodes, and a current source and a current sink connected to each one of the electrodes. The medical device also comprises a calibration arrangement configured to compare the current provided by a selected one of the current sources to the current sunk by a selected one of the current sinks, and configured to adjust an operational parameter of at least one of the source and sink based on said comparison such that the current provided by the selected current source is substantially the same as the current sunk by the current sink.

18 Claims, 3 Drawing Sheets

(56) References Cited

U.S. PATENT DOCUMENTS

2005/0267546 A1* 12/2005 Parramon et al. ............... 607/48
2007/0038250 A1* 2/2007 He et al. ............................ 607/2
2007/0100399 A1 5/2007 Parramon et al.
2007/0135868 A1 6/2007 Shi et al.
2010/0152817 A1* 6/2010 Gillbe .................. A61N 1/0551 607/72

* cited by examiner

CALIBRATION OF CURRENT SOURCES AND SINKS IN A STIMULATING MEDICAL DEVICE

CROSS-REFERENCE TO RELATED APPLICATIONS

This application is a national stage application of PCT Application No. PCT/IB2010/054246, entitled, "Calibration Of Current Sources and Sinks In A Stimulating Medical Device," filed on Sep. 20, 2010, which claims the benefit of Australian Patent Application No. 2009217394, filed Sep. 18, 2009, the contents of these applications being incorporated by reference herein in their entirety.

BACKGROUND

1. Field of the Invention

The present invention relates generally to stimulating medical devices, and more particularly, to calibration of current sources and sinks in a stimulating medical device.

2. Related Art

The delivery of electrical stimulation has become an established part of medical therapy. Numerous types of medical devices have components positioned on, or implantable in, a recipient's body in order to stimulate a recipient's tissue. Such devices are sometimes referred to herein as stimulating medical devices. Stimulating medical devices commonly include a plurality of electrodes that function as the interface between electronics of the device and the recipient's body tissue. In general terms, current is delivered to the recipient's tissue via the electrodes in order to evoke a response, such as a perception (e.g. for sound perception) or a function (e.g. for limb movement), in the recipient.

Figure 1:
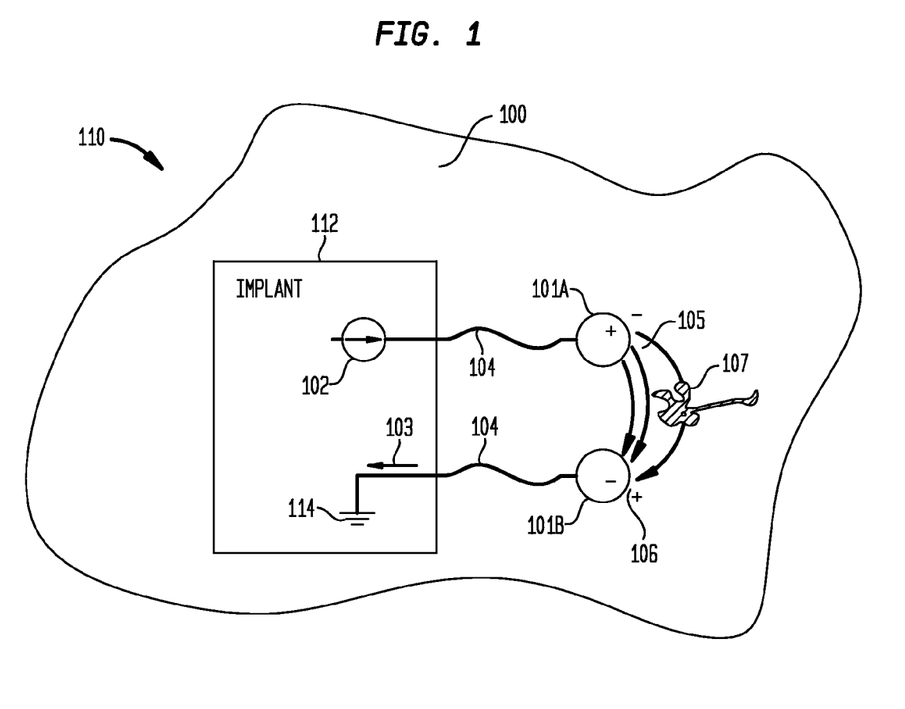
FIG. 1 is a schematic diagram illustrating electrical stimulation of a recipient's tissue via two electrodes.

FIG. 1 is a schematic diagram illustrating the delivery of current to tissue. In this illustration, an implantable stimulating medical device 110 comprises an implantable component 112, and a multi-electrode system in the form of two platinum electrodes 101. Each of the electrodes are connected to component 112 by insulated wires 104. Component 112 comprises a stimulating current source 102 that provides current to electrode 101A. The current passes through the recipient's tissue 100, including nerve cell 107, and returns to ground 114 within implantable component 112. The return of this current is shown schematically by arrow 103.

At the surface of platinum electrodes 101, chemical reactions take place, changing the electron current from the current source to an ion current 105 in the tissue. A charge 106 remains on the electrode surface, causing an increase in voltage in the tissue. Under normal conditions, these chemical reactions are reversible by a change in the direction of current. That is, a reversal in the direction of current will neutralize the increase in voltage. As such, it is common for the stimulation current to be delivered as biphasic pulses, in such a way that there is no net charge delivered to the tissue. A biphasic pulse includes a positive charge pulse followed by an equal negative charge pulse. In certain circumstances, the current level (amplitude) and periods of both the positive and negative pulses are substantially the same. In other circumstances, one of the pulses is applied over a longer or shorter period, but has lower or greater amplitude, respectively. However, in both circumstances, the total charge remaining in the tissue after delivery of both the positive and negative pulses is substantially zero.

In circumstances using biphasic pulses, if current is allowed to flow in one direction for too long, toxic products can escape and damage or destroy the surrounding tissue. Likewise, if the voltage between two electrodes is allowed to remain elevated for too long, toxic species are irreversibly generated. To ensure that stimulation remains safe, and that no toxic species escape, it is known that the DC and low-frequency (LF) states of the electrodes, sometimes referred to as the DC/LF voltages and the DC/LF currents, must remain within certain bounds. For a typical cochlear implant electrode having an area of about 0.25 mm$^2$, these values are generally a few hundred milli-volts (mV), or tens of nano-amperes (nA). Additionally, the United States Federal Drug Administration (FDA) requires that the magnitude of the current through an electrode, during a 1 ms period, be below 100 nA. The use of charge neutralizing biphasic pulses helps ensure that these requirements are met, but charge errors occur in practice.

In certain stimulating medical devices, separate current source circuits and current sink circuits, referred to simply as current sources and current sinks, respectively, are configured to deliver or receive stimulating current. The sources and sinks each use a Digital-to-Analog Converter (DAC) to control the flow of current.

SUMMARY

In one aspect of the present invention, a stimulating medical device is provided. The medical device comprises: a plurality of electrodes; a current source and a current sink connected to each one of the electrodes; and a calibration arrangement configured to compare the current provided by a selected one of the current sources to the current sunk by a selected one of the current sinks, and configured to adjust an operational parameter of at least one of the source and sink based on said comparison such that the current provided by the selected current source is substantially the same as the current sunk by the current sink.

In another aspect of the present invention, a method of calibrating current sources and current sinks in a stimulating medical device, wherein each electrode has a current source and a current sink associated with the electrode is provided. The method comprises: selecting a current source and a current sink; comparing the current provided by the selected current source and the current sunk by the selected current sink; and adjusting an operational parameter of at least one of the source and sink based on the evaluation such that the current provided by the selected current source is substantially the same as the current sunk by the current sink.

BRIEF DESCRIPTION OF THE DRAWINGS

Embodiments of the present invention are described below with reference to the attached drawings, in which.

DETAILED DESCRIPTION

As is known in the art, certain stimulating medical devices are configured to implement current focusing strategies in which particular groups of nerve or tissue cells are stimulated at selected times or stimulated independently of adjacent cells. Additionally, complex stimulation strategies have been developed for certain medical devices that require control of the current delivered and/or the current sunk by electrodes. That is, there is a level of current matching required between current sources and sinks in stimulating medical devices that facilitates effective current focusing and other stimulation strategies. As used herein, current matching refers to matching of the current delivered by a current source to the current sunk by a current sink. Current sources and sinks are referred to as being matched when the current delivered by the source substantially match the current sunk by the sink.

Typically, the current sources and sinks comprise Digital-to-Analog Converter (DACs), and the desired level of current matching is set during manufacture by trimming the DACs. However, setting accuracy during manufacture does not account for the possibility that DACs operational parameters may drift over time. For example, typical silicon IC manufacturing technologies may result in the value of each stimulation current source and sink being susceptible to drift, by different and unpredictable amounts, after implantation into a recipient (potentially tens of years). IC manufacturers generally do not guarantee the drift of crucial parameters beyond a 10-20 year timeframe. Unfortunately, a period of 10-20 years is much less than the typical intended lifetime of a stimulating medical device.

Aspects of the present invention are generally directed to providing the desired level of current matching through in situ calibration of current sources and sinks in a stimulating medical device. More particularly, a stimulating medical device in accordance with aspects of the present invention comprises a plurality of electrodes each connected to a current source and a current sink. Each current source comprises a p-type Digital-to-Analog Converter (PDAC) that sources current from a supply, while each current sink comprises an n-type Digital-to-Analog Converter (NDAC) that sinks current to a ground. The calibration arrangement is configured to compare the current provided by a current source to the current sunk through a current sink. Based on the comparison, the calibration arrangement adjusts the parameters of either the PDAC and NDAC until the sourced and sunk currents are substantially the same.

The in situ calibration of current sources (i.e. subsequent to the manufacturing process) that ensures sufficient current matching between the sources and sinks to facilitate effectiveness of current focusing and other stimulation strategies. The calibration of current sources also helps maintain the safety of the device by reducing the potential for accumulation of harmful toxic products as a result of the mismatching of stimulation currents. The current source and sink calibration of the present invention may reduce, but will likely not eliminate, all toxic products resulting from mismatched current.

Embodiments of the present invention will be described with reference to a particular stimulating medical device, namely an intra-cochlear electrical stimulation system, (commonly referred to as a cochlear prosthetic device, cochlear implant, cochlear device, and the like; simply "cochlear implant" herein.) However, it would be appreciated that embodiments of the present invention may be implemented in any stimulating medical device, including, but not limited to, hybrid electrical and acoustic stimulation systems, brain stem implants, muscle stimulators or other neural stimulation systems. Additionally, it would be appreciated that embodiments of the present invention may be implemented in systems having both implanted and external components, as well as a totally or fully implanted system.

As noted, embodiments of the present invention generally relate to the electrical stimulating components of a cochlear implant. As would be appreciated, cochlear implants also include a variety of signal processors, power supplies, RF links, etc. All of these elements are well known in the art and will not be described in detail herein.

Figure 2:
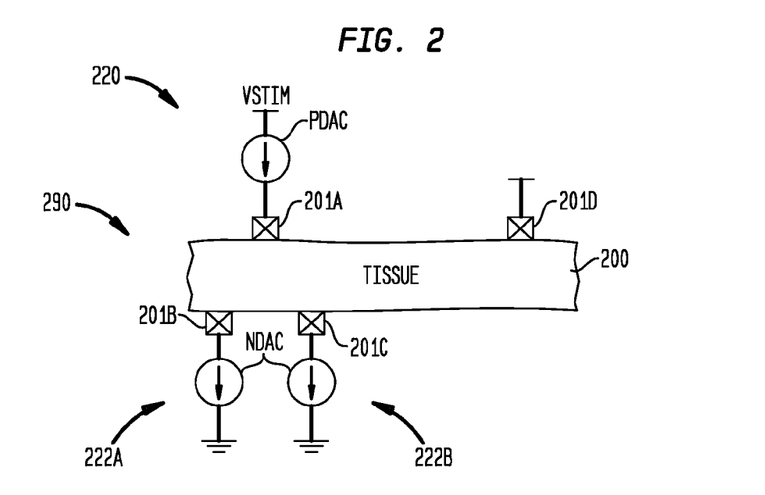
FIG. 2 is a schematic circuit diagram of a multi-electrode system in which one electrode is connected to a current source and two electrodes are connected to current sinks.

FIG. 2 is a schematic diagram of an exemplary cochlear implant 290. As shown, cochlear implant 290 comprises a plurality of electrodes 201 configured to interface with a recipient's tissue 200. As shown, electrode 201A is switchably connected to a current source 220 provided by a p-type digital-to-analog converter (PDAC) connected to a stimulating supply rail $V_{stim}$. The current sourced through PDAC 220 is sunk by current sinks 222A, 222B associated with electrodes 201B, 201C, respectively. Each of the current sinks 222 comprise a n-type digital-to-analog converter (NDAC) connected to ground.

FIG. 2 illustrates cochlear implant 290 having three electrodes. However, it would be appreciated that cochlear implant 290 may include larger numbers of electrodes. For example, in one specific implementation, cochlear implant 290 includes 24 stimulating electrodes. In such an arrangement, each electrode may have a respective PDAC and a NDAC connected thereto. Accordingly, such an arrangement would include a total 48 DACs. Implementations are also envisioned in which fewer DACs are required. For example, implementations may use one or more DACs which are not associated with particular electrodes, but that are selectively connected using suitable switches. The present invention is not limited in application to any one of the above or other DAC configuration.

During normal operation, any number of electrodes may operate to sink or source current at the same time, referred to as asynchronous stimulation. In the specific example of FIG. 2, sourcing current of 1.0 units is provided at electrode 201A. Sinking current of 0.5 units is provided by each of electrode 201B and 201C, thereby reducing the net current (and hence charge) to approximately zero. As previously noted, this current matching is a key issue in maintaining the effectiveness of current focusing and other stimulation strategies.

In certain embodiments, each DAC is individually programmable, under the control of, for example, the system controller or processor, to apply a required stimulation current for the respective electrode. Accordingly, all current DACs should be accurately matched for a given programmable value so that the total current entering and leaving all the electrodes can be programmed as close to zero as possible. In specific implementations, an accuracy of approximately 0.1% between sourced and sunk current is desirable.

Figure 3:
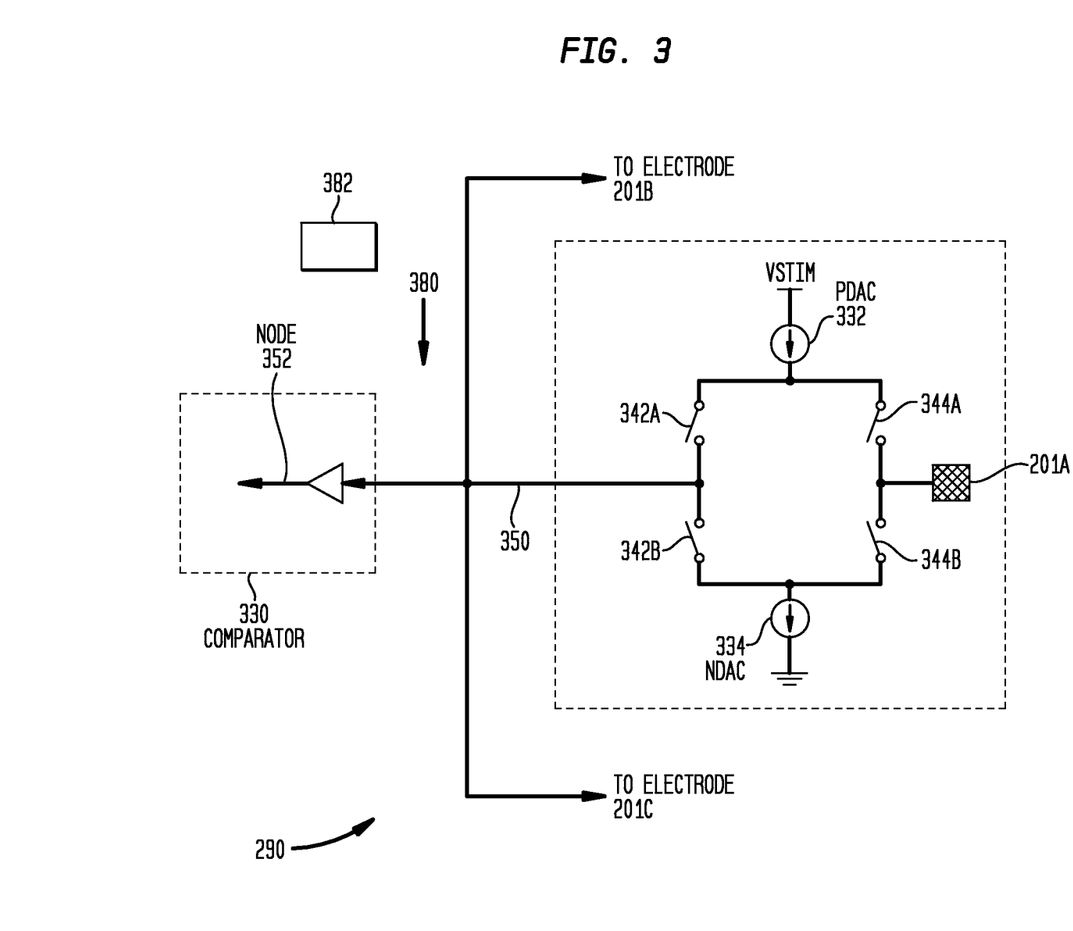
FIG. 3 is a circuit diagram of the multi-electrode system of FIG. 2 including a calibration arrangement, in accordance with embodiments of the present invention.

As previously noted, embodiments of the present invention seek to calibrate all current sources and sinks to ensure they are able to obtain the desired accuracy. FIG. 3 is a schematic diagram illustrating one system for calibrating the sources and sinks of one electrode 201A of cochlear implant 290 of FIG. 2. It would be appreciated that arrangements similar to that shown in FIG. 3 may be provided for each electrode or DAC.

As shown in FIG. 3, electrode 201A is electrically connectable, via switch 344A, to a current source 332 comprising a PDAC connected to a supply voltage ($V_{stim}$). Similarly, electrode 201A is connectable, via switch 344B, to a current sink comprising a NDAC connected to ground. In operation, switches 344 are selectively actuated depending on whether electrode 210A is sinking or sourcing current.

Additionally, cochlear implant 290 of FIG. 3A comprises a calibration arrangement 380. Calibration arrangement 380 comprises, in this embodiment, a comparator 330 connectable to each of PDAC 332 and NDAC 334 via switches 342 and line 350. To perform calibration of either PDAC 332 or NDAC 334, the respective switch 342 is closed to provide a path between the DAC and comparator 330. At the same time, a PDAC or NDAC is also connected to comparator 330 and the resulting current values are evaluated by the comparator.

For example, in one specific implementation, cochlear implant 290 comprises a processor 382 that sets PDAC 332 and an NDAC from electrode 201B each to a high value. That is, assigning bit values to the digital output of each of PDAC 332 and the NDAC, the most significant bit (MSB) of each would be set to a '1' and all other bits would be set to '0'. Additionally, the processor closes the necessary switches to connect each of PDAC 332 and the NDAC to comparator 330. At this time, switches to electrodes 201A, 201B are set open so that no current flows to the electrodes. The currents provided to comparator 330 will result in the voltage at node 352 being pulled towards one of either the supply rail or ground, depending on its sign. More particularly, if the current of PDAC 332 is higher, then the node 352 will pull up to $V_{stim}$, and if the current of NDAC of electrode 201B is higher, then node 352 will pull down to ground. Comparator 330 senses this and transmits a representative signal back to processor 382. As would be appreciated, processor 382 may comprise any combination of hardware or software and may be part of calibration arrangement 380 or may be positioned in a separate implantable or external component. For ease of illustration, processor 382 is shown schematically using a simple block element.

As a result of the comparison, processor 382 will vary either the programmable value of the output of the NDAC of electrode 201B or the output value of PDAC 332 by 1 LSB in the appropriate direction that would cause comparator 330 to change state. For example, if node 352 was high (that is, pulled toward the supply rail), then processor 382 would increase the programmable value of the NDAC of electrode 201B by 1 LSB. Processor 382 continues with the incremental change of the next LSB until the state of comparator 330 changes. DAC operational parameters or settings may be adjusted by altering their trimmed values as well as applying a gain correction factor to their digital programmable values.

Once the state of comparator 330 changes, the amount by which the programmable value of the NDAC of electrode differs from the value of PDAC 332 is stored. This value may be stored in non-volatile memory (NVM) within the implanted device, in an external component, or in a separate device such as a remote control. This value may then be used by elements of the device that control stimulation to correct for the gain error between the two evaluated DACs.

The steps discussed above for PDAC 332 and the NDAC of electrode 201B may be repeated for the NDACs in comparison to PDAC 332 (including the NDAC of electrode 201A). Processor 382 may then repeat the steps for all of the PDACs of the other electrodes versus the NDACs. In these subsequent tests, the calibration value for the NDAC of electrode 201B is used.

In certain implementations, processor 382 will compare the current for NDAC 334 of electrode 201A to an arbitrarily chosen PDAC of the same or different electrode. This comparison uses the (calibration value for the arbitrarily selected PDAC). Similarly, processor 382 will compare the current for a PDAC of another electrode to that of any arbitrarily chosen NDAC of another electrode. Again this comparison uses calibration value for the arbitrarily selected NDAC. The result of these two additional steps is that a correction value is generated. This correction value may be stored in memory for all DACs, except for PDAC 332, and may be used to control the stimulation currents as a gain error correction value that should be applied to the programmable value for each DAC.

In the above exemplary implementation, all DACs are calibrated for the purpose of matching relative to a single selected DAC. As would be appreciated, the selected reference DAC may itself be subject to drift from the initial value set at manufacture. As such, the above method does not address a recalibration of absolute values of the DACs, but rather provides a relative calibration between the DACs. However, it is noted that this relative matching suitably satisfies the aspect of stimulation current matching for current focusing and other stimulation strategies.

As would be appreciated, the arrangement and method described above with reference to FIG. 3 is merely illustrative, and other arrangements/methods for calibrating current sources and sinks are within the scope of the present invention. For example, in one alternative implementation, the method commences, as above, with an NDAC and PDAC being compared to one another. In this variation, the digital current values for each of the NDAC and PDAC are set such that the most significant bits (MSB) are high, while the other bits are set low (e.g. 10000). In these embodiments, if, for example, the PDAC value is higher, the value of the NDAC may remain fixed, and the MSB, rather than the LSB as described above, of the PDAC bit value may be adjusted based on the comparison to the predetermined value. More particularly, if PDAC is higher, then the MSB of the PDAC is set to 0. The next MSB is then set to 1 to provide a bit value (starting with the illustrative digital value of 10000) of PDAC=010000. A comparison between the currents is then made (i.e. NDAC=10000 and PDAC=01000). If, as a result of the comparison, the PDAC is still higher, the second MSB is also set to 0. However, if the NDAC is lower, (i.e. the comparator changed state), then the second MSB remains at 1. This process is continued for all bit values assigning either a 1 or 0 to the next MSB of the PDAC. This process, referred to as a successive approximation algorithm, allows the correct value to be determined with no more steps than there are bits (i.e. 11 bits requires 11 iterations).

Figure 4:
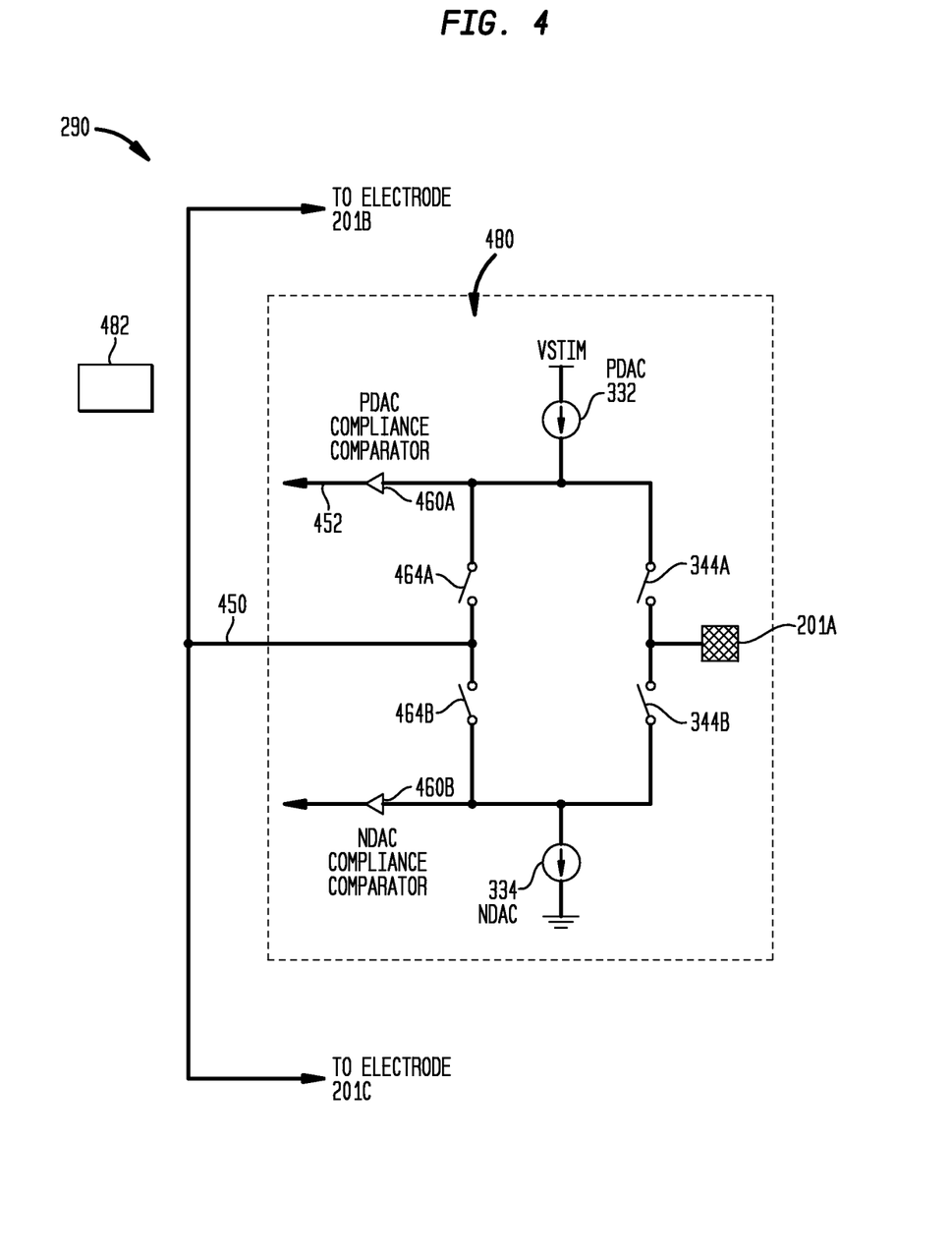
FIG. 4 is a circuit diagram of the multi-electrode system of FIG. 2 including an alternative calibration arrangement, in accordance with embodiments of the present invention.

The arrangement illustrated above with reference to FIG. 3 utilizes an independent comparator shared with all of the DACS. In another exemplary implementation, a comparator associated with, provided as part of a DAC, or otherwise within the stimulation circuitry may be used to perform the comparison. FIG. 4 is a schematic diagram of one alternative system for calibrating the sources and sinks of an electrode 201A of cochlear implant 290 of FIG. 2. In contrast to the embodiments of FIG. 3, the arrangement of FIG. 4 does not use the same comparator for all comparisons.

Similar to the embodiments of FIG. 3, electrode 201A is electrically connected to PDAC 332 and switch 344A. Similarly, electrode 201A is connected to NDAC 334 and switch 344B. In operation, switches 344 are selectively actuated depending on whether electrode 201A is sinking or sourcing current.

PDAC 332 is connected to a PDAC compliance comparator 460A, while NDAC 334 is connected to NDAC compliance comparator 460B. Additionally, switch 464A is configured to selectively connect PDAC 332 and PDAC compliance comparator 460A to a line 450, while switch 464B is configured to connect NDAC 334 and NDAC compliance comparator 460B to line 450. Line 450 extends to other electrodes 201B and 201C.

To perform an exemplary calibration, switches 344A, 344B and 464B are set open, while switch 464A is closed to connect PDAC 332 and PDAC compliance comparator 460A to, for example, an NDAC in electrode 201B. The difference in the currents provided to comparator 460A from PDAC 332 and the NDAC in electrode 201B results in the voltage at node 452 being pulled towards one of either the supply rail or ground, depending on its sign. For example, if the current of PDAC 332 is higher, then node 452 will pull up to $V_A$, and if the current of NDAC of electrode 201B is higher, then node 452 will pull down to ground. Comparator 460A senses this and transmits a representative signal back to a processor 482.

As a result of the comparison, processor 482 will vary either the programmable value of the NDAC of electrode 201B or the value of PDAC 332 by 1 LSB in the appropriate direction that would cause comparator 460A to change state. For example, if node 452 was high (that is, pulled toward the supply rail), then processor 482 would increase the programmable value of the NDAC of electrode 201B by 1 LSB. Processor 482 continues with the incremental change until the state of comparator 460A changes.

Once the state of comparator 460A changes, the amount by which the programmable value of the NDAC of electrode differs from the value of PDAC 332 is stored. This value may be stored in non-volatile memory (NVM) within the implanted device, in an external component, or in a separate device such as a remote control. This value may then be used by the elements that control stimulation to correct for the gain error between the two evaluated DACs.

The steps discussed above for PDAC 332 and the NDAC of electrode 201B may be repeated for the NDACs in comparison to PDAC 332 (including the NDAC of electrode 201A). Processor 482 may then repeat the steps for all of the PDACs of the other electrodes versus the NDACs. In these subsequent tests, the calibration value for the NDAC of electrode 201B is used.

In certain implementations, processor 482 will compare the current for NDAC 334 of electrode 201A to an arbitrarily chosen PDAC in substantially the same manner as described above. This comparison uses the calibration value for the arbitrarily selected PDAC. Similarly, processor 482 will compare the current for a PDAC of another electrode to that of any arbitrarily chosen NDAC of another electrode. Again this comparison uses calibration value for the arbitrarily selected NDAC. The result of these two additional steps is a correction value is generated. This correction value may be stored in memory for all DACs, except for PDAC 332 and may be used to control the stimulation currents as a gain error correction value that should be applied to the programmable value for each DAC.

In specific implementations of FIGS. 3 and 4, it is possible to implement comparisons of DACS within different zones or areas of the electrode array. That is, the system may perform localized calibrations in which DACS of certain area of the electrode array are compared only to DACS within that same area, rather than to all the DACS within the electrode array. Depending on the hardware configuration of the system, these localized calibrations may be performed sequentially (i.e. calibrate the DACS of one area after one another) or simultaneously (performance of multiple localized calibrations at the same time). Sequential comparisons may use a single common comparator, or multiple comparators, depending on the desired configuration, while simultaneous comparisons use multiple comparators.

Additionally, FIGS. 3 and 4 have been described with reference to a comparator to evaluate the currents of a current source and sink. In one alternative embodiment, the current comparator may be replaced by a resistor and analog-to-digital converter (ADC). In such an embodiment, instead of diverting two currents to the line connecting the comparator, PDAC and NDAC (lines 350 and 450 in FIGS. 3 and 4) currents could be sequentially diverted to the resistor and the voltage on the line measured by the ADC. The sequentially recorded ADC values could be compared to determine the difference in current.

In the above embodiments, the calibration path is generally independent of the electrode current path. Accordingly, the calibration does not depend upon, for example, the peculiarities of location, orientation or connection of the electrode, or on any electrical effects from such peculiarities.

In another variation, a single PDAC could be calibrated against a single NDAC and the determined calibration values are assumed to apply to all the rest of the PDACs. Such an implementation would simplify both the processing and circuitry. In specific embodiments, the processor is an intelligent controller controls the system and the calibration procedure. The intelligent controller may comprise any combination of hardware/software and may be embedded in an implanted component, such as a stimulator unit, in an external component or other device, such as remote control, fitting system, etc. Additionally, as noted above, a memory allows the calibration data to be stored and accessed when needed.

As previously noted, each DAC includes a digital value comprised of a plurality of bits. It would be appreciated that the least significant bit (LSB) should have a value that is smaller that desired current matching accuracy. If the LSB of the DACs are not smaller than the desired accuracy, then it may be difficult or even impossible to achieve a desired accuracy. Specifically, if the desired current matching accuracy is 1%, then the LSB of the DACs should have a value equal to approximately 0.5% of the desired accuracy.

It will be appreciated that the above calibration procedures may be adjusted for the specific device or recipient. For example, it is not uncommon that one or more electrodes in a cochlear implant are non-functional or are not required for stimulation. As such, any DAC specifically associated with such an electrode need not be calibrated.

As noted above, there area number of different methods for managing the comparison process other than those described above. For example, the number that is recorded in the memory for each DAC pair could be the ratio of the two digital values at the moment when the current comparator changes in sign.

It is noted that it is anticipated that this calibration process will only be carried out infrequently, for example at periodic appointments for maintenance, in response to a fault condition, or the like. Accordingly, the calibration can be performed at a time when it is not required that the stimulating device is operating, and so the user need not be inconvenienced. It is expected that the rate of drift will be relatively slow.

Further features and advantages of the present invention are described in Australian Patent Application No. 2009217394, filed Sep. 18, 2009. This application is hereby incorporated by reference herein.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A stimulating medical device, comprising:
   a plurality of electrodes;
   a plurality of current sources and a plurality of current sinks, wherein each one of the electrodes is connected to at least one of the plurality current sources and to at least one of the plurality of current sinks;
   a calibration arrangement configured to compare the current sourced by a selected one of the plurality of current sources to the current sunk by a selected one of the plurality of current sinks; and
   a processor configured to:
      based on the comparison, iteratively adjust an operational parameter of either the selected current source or the selected current sink until the current sourced by the selected current source is substantially the same as the current sunk by the selected current sink, and
      store a value representing an amount by which the operational parameter of the either the selected current source or the selected current sink was adjusted to make the sourced and sunk currents substantially the same.

2. The medical device of claim 1, further comprising:
   memory, wherein the value is stored in the memory for subsequent use in delivering stimulation signals using the selected current source or the selected current sink.

3. The medical device of claim 2, wherein the plurality of electrodes are configured to deliver electrical stimulation current to a recipient of the medical device, and wherein the medical device is configured to utilize the value stored in the memory during generation of electrical stimulation in order to correct for the gain error between the selected current source and the selected current sink.

4. The medical device of claim 1, wherein each of the plurality of current sources comprises a p-type Digital-to-Analog Converter (PDAC), and wherein each of the plurality of current sinks comprises a n-type Digital-to-Analog Converter (NDAC).

5. The medical device of claim 4, wherein the operational parameter of a DAC is the digitally controlled output of the DAC having a multi-bit value, and wherein the processor is configured to iteratively adjust the multi-bit value of either the selected current source or the selected current sink such that their respective DAC values are within the least significant bit of one another.

6. The medical device of claim 1, wherein the processor is configured to compare the current sunk by the selected current sink to a calibration value representing the current sourced by an arbitrarily chosen current source.

7. The medical device of claim 6, wherein the processor is configured to:
   compare the current sourced by the selected current source to a calibration value representing the current sunk by an arbitrarily chosen current sink; and
   generate, based on the comparison of the current sunk by the selected current sink to the calibration value representing the current sourced by the arbitrarily chosen current source and based on the comparison of the current sourced by the selected current source to the calibration value representing the current sunk by the arbitrarily chosen current sink, a correction value for use in the generation of electrical stimulation.

8. The medical device of claim 1, wherein the calibration arrangement comprises at least one comparator.

9. The medical device of claim 1, wherein the calibration arrangement further comprises:
   a resistor and analog-to-digital converter (ADC) configured to compare the current sourced by the selected current source to the current sunk by the selected current sink.

10. The medical device of claim 1, wherein the processor is included within the calibration arrangement.

11. The medical device of claim 1, wherein the processor is configured to:
    determine the selected current source among the plurality of current sources that is to be selected for the comparison;
    determine the selected current sink among the plurality of current sinks that is to be selected for the comparison;
    select the selected current source by causing a first switch to close corresponding to the selected current source; and
    select the selected current sink by causing a second switch to close corresponding to the selected current sink.

12. A method of calibrating current sources and current sinks in a stimulating medical device comprising a plurality of electrodes, a plurality of current sources, and a plurality of current sinks, wherein each one of the plurality of electrodes is associated with at least one of the plurality current sources and with at least one of the plurality of current sinks, the method comprising:
    selecting a current source and a current sink;
    comparing the current sourced by the selected current source to the current sunk by the selected current sink;
    based on the comparison, iteratively adjusting an operational parameter of either the selected current source or the selected current sink until the current provided by the selected current source is substantially the same as the current sunk by the current sink; and
    storing a value representing an amount by which the operational parameter of the either the selected current source or the selected current sink was adjusted to make the sourced and sunk currents substantially the same.

13. The method of claim 12, further comprising:
    storing the value in memory of the stimulating medical device for subsequent use in delivering stimulation signals using the selected current source or the selected current sink.

14. The method of claim 12, wherein each of the plurality of current sources comprises a p-type Digital-to-Analog Converter (PDAC), and wherein each of the plurality of current sinks comprises a n-type Digital-to-Analog Converter (NDAC).

15. The method of claim 14, wherein the operational parameter of a DAC is the digitally controlled output of the DAC having a multi-bit value, and wherein iteratively adjusting an operational parameter of either the selected current source or the selected sink comprises:
    adjusting the least significant bit of that output value of at least one of the selected current source or the selected current sink so that the current sourced by the selected current source and the current sunk by the selected current sink are substantially the same.

16. The method of claim 12, wherein further comprising:
    comparing the current sunk by the selected current sink to a calibration value representing the current sourced by an arbitrarily chosen current source;
    comparing the current sourced by the selected current source to a calibration value representing the current sunk by an arbitrarily chosen current sink; and
    generating, based on the comparison of the current sunk by the selected current sink to the calibration value representing the current sourced by the arbitrarily chosen current source and based on the comparison of the current sourced by the selected current source to the calibration value representing the current sunk by the arbitrarily chosen current sink, a correction value for use in the generation of electrical stimulation.

17. The method of claim 12, the medical device comprises a resistor and an analog-to-digital converter (ADC), and wherein comparing the current sourced by the selected current source to the current sunk by selected current sink comprises:
- sequentially diverting the current sourced by the selected current source and the current sunk by the selected current sink to the resistor;
- measuring the voltage with the ADC during each sequential diversion; and
- comparing the measured voltages to determine the difference in currents.

18. The method of claim 12, further comprising:
- selecting a second current source and a second current sink;
- comparing, with a comparator, the current sourced by the second selected current source with the current sunk by the second selected current sink; and
- repeating the selection of current sources and sinks and the comparison of currents until a desired number of current sources and sinks have been compared.

* * * * *